United States Patent
Naganuma et al.

(10) Patent No.: US 9,230,170 B2
(45) Date of Patent: Jan. 5, 2016

(54) PLANT SPECIES IDENTIFICATION APPARATUS AND METHOD

(71) Applicant: FUJITSU LIMITED, Kawasaki-shi, Kanagawa (JP)

(72) Inventors: Yasuo Naganuma, Atsugi (JP); Katsuji Ebisu, Kanagawa (JP)

(73) Assignee: FUJITSU LIMITED, Kawasaki (JP)

( * ) Notice: Subject to any disclaimer, the term of this patent is extended or adjusted under 35 U.S.C. 154(b) by 151 days.

(21) Appl. No.: 14/097,344

(22) Filed: Dec. 5, 2013

(65) Prior Publication Data

US 2014/0093138 A1 Apr. 3, 2014

Related U.S. Application Data

(63) Continuation of application No. PCT/JP2012/066608, filed on Jun. 28, 2012.

(30) Foreign Application Priority Data

Jun. 29, 2011 (JP) ................................. 2011-144050

(51) Int. Cl.
*G06K 9/00* (2006.01)
*G01N 21/84* (2006.01)
*G01N 21/17* (2006.01)

(52) U.S. Cl.
CPC ............ *G06K 9/00657* (2013.01); *G01N 21/84* (2013.01); *G01N 2021/1797* (2013.01); *G01N 2021/8466* (2013.01)

(58) Field of Classification Search
CPC .................................................. G06K 9/00657

USPC .......................................................... 382/110
See application file for complete search history.

(56) References Cited

U.S. PATENT DOCUMENTS

| 5,809,164 A * | 9/1998 | Hultgren, III ................. 382/162 |
| 8,805,083 B1 * | 8/2014 | Sieracki ........................ 382/191 |
| 2004/0149893 A1 * | 8/2004 | Scott ............................. 250/221 |

(Continued)

FOREIGN PATENT DOCUMENTS

| JP | 11-283012 | 10/1999 |
| JP | 2006-085517 | 3/2006 |
| JP | 2006-285310 | 10/2006 |

(Continued)

OTHER PUBLICATIONS

Using Vegetation Reflectance Variability for Species Level Classification of Hyperspectral Data. M.A. Cochrane. 2000.*

(Continued)

*Primary Examiner* — Stephen R Koziol
*Assistant Examiner* — Delomia L Gilliard
(74) *Attorney, Agent, or Firm* — Fujitsu Patent Center

(57) ABSTRACT

A plant species identification apparatus for identifying plant species is disclosed. A reference data storage part stores reference spectral data which indicate a reflectance spectral feature classified by area segments including a sunlit portion and a shaded portion in addition to the plant species. A data input part acquires hyperspectral data to be a target. A determination part specifies the reflectance spectral feature of a pixel for each of pixels of the hyperspectral data from the reference data storage part and to determine the plant species of the pixels based on a classification of the reference spectral data.

7 Claims, 11 Drawing Sheets

(56) References Cited

U.S. PATENT DOCUMENTS

2008/0046217 A1   2/2008   Polonskiy et al.
2009/0171591 A1*  7/2009   Timmis et al. .................. 702/19

FOREIGN PATENT DOCUMENTS

| JP | 2008-161157   |   | 7/2008 |
|----|---------------|---|--------|
| JP | 2010-086276   |   | 4/2010 |
| JP | 2010086276 A  | * | 4/2010 |
| JP | 2011-103098   |   | 5/2011 |

OTHER PUBLICATIONS

Mapping urban forest tree species using IKONOS imagery: preliminary results. Ruiliang Pu. Feb. 2010.*

Hyperspectral discrimination of tropical rain forest tree species at leaf to crown scales. Matthew L. Clark, Dar A. Roberts, David B. Clark. Mar. 2005.*

Eiji Kaneko et al., "Estimation of Solar Spectrum in Cloudy Condition", 2011 Nen The Institute of Electronics, Information and Communication Engineers Sogo Taikai Koen Ronbunshu, Feb. 28, 2011, Joho System 2, p. 76.

Masato Kato, et al., "2. Hyper Spectrum no Riyo 2.3 Kokuki Hyper Data ni yoru Shin'yoju Kubun", Journal of the Japan Society of Photogrammetry and Remote Sensing, Nov. 2, 2007, vol. 46, No. 5, pp. 19 to 24.

Masato Kato, "Bunko Hoshakei ni yoru Shin'yoju 12 Shu no Hansha Spectrum Tokusei", Transactions of The Japanese Forestry Society, Mar. 20, 2004, Dai 115 Kai, p. 185.

International Search Report, mailed in connection with PCT/JP2012/066608 and mailed Oct. 2, 2012.

Clark, M L et al: "Hyperspectral discrimination of tropical rain forest tree species at leaf to crown scales", Remote Sensing of Environment, Elsevier, XX, vol. 96, No. 3-4, Jun. 30, 2005, pp. 375-398, XP027794685, ISSN: 0034-4257 [retrieved on Jun. 30, 2005] pp. 375-383.

Ruiliang Pu: "Mapping urban forest tree species using IKONOS imagery: preliminary results", Environmental Monitoring and Assessment; An International Journal Devoted to Progress in the Use of Monitoring Data in AssessingEnvironmental Risks to Man and the Environment, Kluwer Academic Publishers, DO, vol. 172, No. 1-4, Feb. 6, 2010, pp. 199-214, XP019866875, ISSN: 1573-2959, DOI: 10.1007/S10661-010-1327-5.

EESR—Extended European Search Report mailed on Nov. 7, 2014 issued with respect to the corresponding European Patent Application No. 12805076.2.

CNOA—Office Action dated Mar. 10, 2015 issued with respect to the corresponding Chinese Patent Applicaiton No. 201280030019.X, with partial English translation.

* cited by examiner

FIG.6

| PLANT SPECIES | REGION SEGMENT | NUMERICAL VALUE DERIVED FROM FEATURE POINT ||||
| --- | --- | --- | --- | --- | --- |
| | | = A/C | = CB/AB | = (A/B)/(A/C) | = (CB/CD)/(CD/CE) |
| PLANT A | IN SUN | ○○○ | △△△ | ××× | □□□ |
| | IN MIXED LIGHTING CONDITION | ○○○ | △×△ | ×○× | □□□ |
| | IN SHADE | ○○× | △△○ | △×× | □□× |
| PLANT B | IN SUN | ○○○ | ××× | □□□ | △△△ |
| | IN MIXED LIGHTING CONDITION | ○○○ | △×△ | ×○× | □□□ |
| | IN SHADE | △○△ | △△△ | ××× | □□△ |
| ... | | ... | ... | ... | ... |

FIG.7A

| | A/C | CB/AB | (A/B)/(A/C) | BC·BE/BD^2 |
|---|---|---|---|---|
| JUGLANS MANDSHURICA | 1.49 | 1.59 | 4.01 | 2.28 |
| ROBINIA | 1.20 | 1.27 | 3.01 | 6.03 |
| FIRMIANA SIMPLEX | 1.99 | 2.24 | 2.46 | 2.96 |
| CINNAMOMUM CAMPHORA | 1.58 | 1.77 | 2.62 | 1.97 |
| QUERCUS MYRSINIFOLIA | 2.01 | 2.20 | 3.14 | 1.24 |
| GINKGO BILOBA | 0.97 | 0.96 | 6.14 | 1.83 |
| DAPHNIPHYLLUM MACROPODUM | 1.73 | 1.89 | 3.10 | 2.22 |
| CEDRUS DEODARA | 1.15 | 1.20 | 3.90 | 2.70 |
| OSMANTHUS FRAGRANS VAR. AURANTIACUS | 2.11 | 2.62 | 1.51 | 2.51 |
| CERASUS SPACHIANA 'PENDULA' | 1.06 | 1.11 | 2.34 | 3.90 |
| ZELKOVA SERRATA | 1.56 | 1.73 | 2.84 | 2.66 |
| TERNSTROEMIA GYMNANTHERA BEDDOME | 2.65 | 3.15 | 1.63 | 2.27 |
| PRUNUS YEDOENSIS | 1.57 | 1.73 | 2.95 | 2.34 |

FIG.7B

| | | D/A | (D-C)/(B-C) | (B/C)/(D/B) | (B-A)/(D-A) |
|---|---|---|---|---|---|
| PINUS THUNBERGII | IN SUN | 34.14 | 7.51 | 0.46 | 0.26 |
| | IN 50% MIXED LIGHTING CONDITION | 24.47 | 9.16 | 0.41 | 0.25 |
| | IN SHADE | 14.22 | 19.79 | 0.31 | 0.21 |
| CHAMAECYPARIS LAWSONIANA | IN SUN | 46.41 | 9.78 | 0.38 | 0.15 |
| | IN 50% MIXED LIGHTING CONDITION | 30.61 | 10.88 | 0.33 | 0.15 |
| | IN SHADE | 18.67 | 26.14 | 0.21 | 0.13 |

US 9,230,170 B2

PLANT SPECIES IDENTIFICATION APPARATUS AND METHOD

CROSS-REFERENCE TO RELATED APPLICATION

This patent application is a continuation application of International Application PCT/JP2012/066608 filed on Jun. 28, 2012 and designated the U.S., which claims priority to Japanese Patent Application No. 2011-144050, filed in Japan on Jun. 29, 2011. The entire contents of the foregoing applications are incorporated herein by reference.

FIELD

The present invention is related to an identification technology of plant species in a vegetation survey using remote sensing from a satellite or an aircraft.

BACKGROUND

In conventional vegetation survey methods, there are mainly two methods. In a first survey method, an identification person surveys a location of plants on foot, and visually determines situations at the location. A second survey method is a method (remote sensing) in which the identification person discriminates the plants by using photographs and images captured by a satellite or an aircraft. These methods are used separately or by combining them.

A sensor using the remote sensing of the second survey method used to be panchromatic (black and white). Recently, a type of the sensor has been changing to be multispectral (colors). Hence, a specialist (identification person) investigates multispectral photographs and images, and the vegetation is identified.

Also, recently, creation of a vegetation map using a Geographic Information System (GIS) has been mainstream. In the GIS, Normalized Difference Vegetation Index (NDVI) is used as reference information, which is prepared beforehand and indicates a crown shape of color for each of plant species, and the plant species are discriminated by conducting pattern matching for the images captured by a camera or the sensor.

Also, in recent years, a satellite (satellite name: EO-1 (sensor name: Hyperion), satellite name: PROBA (sensor name: CHRIS)) mounting a hyperspectral sensor capable of measuring a band, which is ten times more than a conventional multispectral sensor, was launched as a global environmental satellite or the like, and measurement is performed by the hyperspectral sensor. An information amount acquired by using the hyperspectral sensor is dramatically improved. Also, an airborne hyperspectral sensor has been developed, and has begun to be utilized in various fields including environmental and agricultural fields.

Furthermore, as a conventional method of tree species discrimination, a method is known in which image data indicating a forest current state are divided into small segments and the tree species are determined for each of the small segments of the image data. Also, another method is known in which multiple sets of band data are acquired based on an proper time for analysis of the tree species, a mask process is performed for NDVI for each of the tree species by generating a target extraction map for each of the tree species in which an upper and lower limit values are set for a luminance value for each set of the band data, and a tree species distribution is extracted.

A further method is known in which luminance values of the image data of a forest taken from the sky are planarized at peaks and valleys, an area is divided depending on a space change of the luminance values of the image data being planarized, the crown shape and its texture feature amount are calculated, and the tree species is determined based on the texture feature amount of an existing crown.

RELATED-ART DOCUMENTS

Patent Documents

Patent Document 1: Japanese Laid-Open Patent Publication No. 2010-086276
Patent Document 2: Japanese Laid-Open Patent Publication No. 2006-085517
Patent Document 3: Japanese Laid-Open Patent Publication No. 2006-285310

OVERVIEW OF THE INVENTION

Problems to be Solved by the Invention

By acquiring information by using the hyperspectral sensor (hyperspectral camera), it is possible to acquire a larger amount of information than with the conventional multispectral sensor.

Hyperspectral data acquired by the hyperspectral sensor include spectral data including wavelength information and light intensity information for each coordinate (for each pixel) in an image. It may be said that the hyper spectral data correspond to data of a three dimensional structure having an element as the spectral data in a two dimensional element as an image. Accordingly, by matching the hyperspectral data with NDVI to be a reference, it also becomes possible to classify a plant species.

However, since accuracy of the hyperspectral data of plants is higher than the conventional multispectral data, the accuracy greatly changes depending on the acquisition state. Thus, it is important how to manage reference data. For example, the spectral data of the plants change depending on an acquisition term and time (season) of data. It is possible to correct the conventional multispectral data by using reference data corresponding to the time (season) at which a matching target was acquired, or by standardizing data.

However, since the hyperpectral data are acquired with a more precise band more than the multispectral data, a spectrum is different between a sunlit portion exposed by sunlight and a shady portion being shaded by other leaves and branches. Hence, since permeability in a visible light region is different from that in a near-infrared light, even if an intensity correction is conducted by an existing maximum value standardization, the spectrum of the sunlit portion does not correspond to that of the shaded portion.

Therefore, in a case of identifying the plant species by using the hyperspectral data for a vegetation survey, it is difficult to precisely classify the plant species in the shaded portion. Thus, the plant species have not been classified in the shaded portion or the plant species have been misclassified as another plant. Accordingly, as a result, in a semi-automatic plant species identification process, there is a problem in which precise plant classification may be degraded.

Therefore, since a size of one pixel is smaller in the hyperspectral data acquired by measuring on ground level or from a relatively low altitude, there is no problem. In a case of the hyperspectral data taken from an artificial satellite or a relatively high altitude, there are included pixels corresponding to an area mixing the sunlit portion and the shaded portion. Accordingly, even if the spectral data of the sunlit portion and the shaded portion are used, there is a problem in which it is not possible to determine the plant species.

SUMMARY

According to one aspect of an embodiment, there is provided a plant species identification apparatus for identifying plant species, the apparatus including a processor configured to perform a process including: a reference data storage part configured to store reference spectral data which indicate a reflectance spectral feature classified by area segments including a sunlit portion and a shaded portion in addition to the plant species; a data input part configured to acquire hyperspectral data to be a target; and a determination part configured to specify the reflectance spectral feature of a pixel for each of pixels of the hyperspectral data from the reference data storage part and to determine the plant species of the pixels based on a classification of the reference spectral data.

The object and advantages of the invention will be realized and attained by means of the elements and combinations particularly pointed out in the appended claims.

It is to be understood that both the foregoing general description and the following detailed description are exemplary and explanatory and are not restrictive of the invention as claimed.

Effects of the Invention

According to a disclosed plant species identification apparatus, even in a case in which hyperspectral data include a sunlit portion and the shaded portion, it is possible to easily identify the plant species without being subject to experience of an accomplished identification person.

BRIEF DESCRIPTION OF DRAWINGS

FIG. 6 is a diagram illustrating an example of a numeric value set of the reference spectral data.

FIG. 7A and FIG. 7B are diagrams illustrating concrete examples of numeric value sets of the reference spectral data for each of plant species.

DESCRIPTION OF EMBODIMENT

In the following, a plant species identification apparatus disclosed as one aspect of the present invention will be described.

In the present invention, there are provided an apparatus, a method, and a program in which in a case of identifying the plant species by using the hyperspectral data, the plant species are appropriately identified from data including the sunlit portion and the shaded portion.

Figure 1:
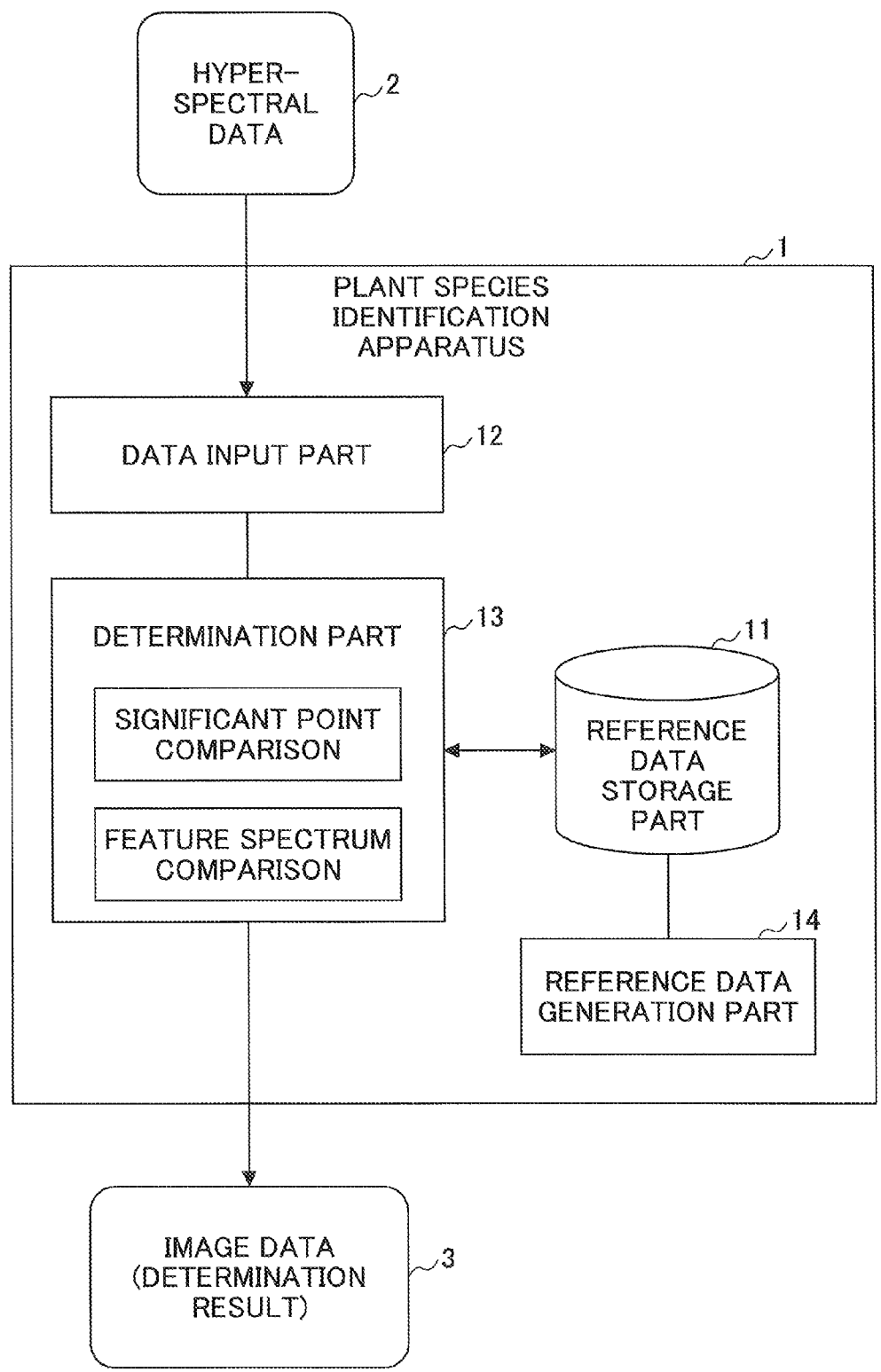
FIG. 1 is a diagram illustrating a configuration example of a plant species identification apparatus in an embodiment.

FIG. 1 is a diagram illustrating a configuration example of the plant species identification apparatus in an embodiment.

A plant species identification apparatus 1 inputs hyperspectral data (hyperspectral image data) of an identification target, which were taken by a hyperspectral sensor or a hyperspectral camera, and identifies a plant species of the identification target.

The plant species identification apparatus 1 includes a reference data storage part 11, a data input part 12, a determination part 13, and a reference data generation part 14.

The reference data storage part 11 stores reference spectral data being reflectance spectral data which are classified for each of the plant species and area segments.

The plant species corresponds to types of plants to be identification targets.

The area segments are regarded as segments of areas which are classified depending on a degree of exposing light from a light source (such as the sun). The area segments include a sunlit portion corresponding to an area in the sun and a shaded portion corresponding to an area in the shade due to other leaves and branches. Also, the area segments include a mixed portion corresponding to an area where the sunlit portion and the shaded portion are mixed. Reference spectral data are generated by the reference data generation part 14 which will be described, and stored in the reference data storage part 11.

The data input part 12 inputs the hyperspectral data 2 acquired by the hyperspectral sensor or the hyperspectral camera.

For the reflectance spectral data of the hyper spectral data 2 being input, it is preferable that a value with respect to a wavelength of the hyperspectral data is a value of such as relative reflectance, maximum normalized relative reflectance, or the like.

The determination part 13 specifies the reference spectral data matching a feature of the reflectance spectral data of a pixel from multiple sets of the reference spectral data stored in the reference data storage part 11 for each of pixels of the hyperspectral data 2 being input. The determination part 13 determines the plant species of an extracted pixel or the plant species and area segments based on classification (the plant species and the area segment) of the specified reference spectral data. As a result, the determination part 13 outputs image data 3 where a determination result (the plant species, or the plant species and area segment) for each of pixels in an image of the hyperspectral data 2 is mapped.

The determination part 13 is able to determine a suitable reference spectral data by performing two determination methods described below.

As a first determination method, the determination part 13 extracts feature points from each set of the reference spectral data stored in the reference data storage part 11, and acquires a numeric value set by calculating multiple predetermined arithmetic expressions. After that, the determination part 13 extracts the feature points from the reflectance spectral data of a pixel for each of pixels which are extracted from the hyperspectral data 2, acquires the numeric value set by calculating the same arithmetic expressions, compares the numeric values set of the pixel with the numeric value set for each set of the reference spectral data, and specifies the reference spectral data having a most similar numeric value set.

Alternatively, as a second determination method, the determination part 13 acquires a feature vector for each set of the reference spectral data stored in the reference data storage part 11. Also, the determination part 13 acquires the feature vector of the reflectance spectral data of pixels extracted from the hyperspectral data 2, and compares the feature vector of the spectral data of the pixels with the feature vector for each sets of the reference spectral data.

The reference data generation part 14 regards, as teacher data, the reference spectral data (the reflectance spectral data) which are for the same plant species and in which the sunlit portion and the shaded portion are included in the area segment, and predicts the reflectance spectral data of the area mixing the sunlit portion and the shaded portion at a predetermine ratio. The reference data generation part 14 adds the predicted reflectance spectral data as the reference spectral data which are for the same plant species and in which the area segment corresponds to the mixed portion, into the reference data storage part 11. The reference data generation part 14 may appropriately change the ratio at which the sunlit portion is mixed with the shaded portion, and may predict the reference spectral data concerning the mixed portion at an arbitrary ratio.

Figure 2:
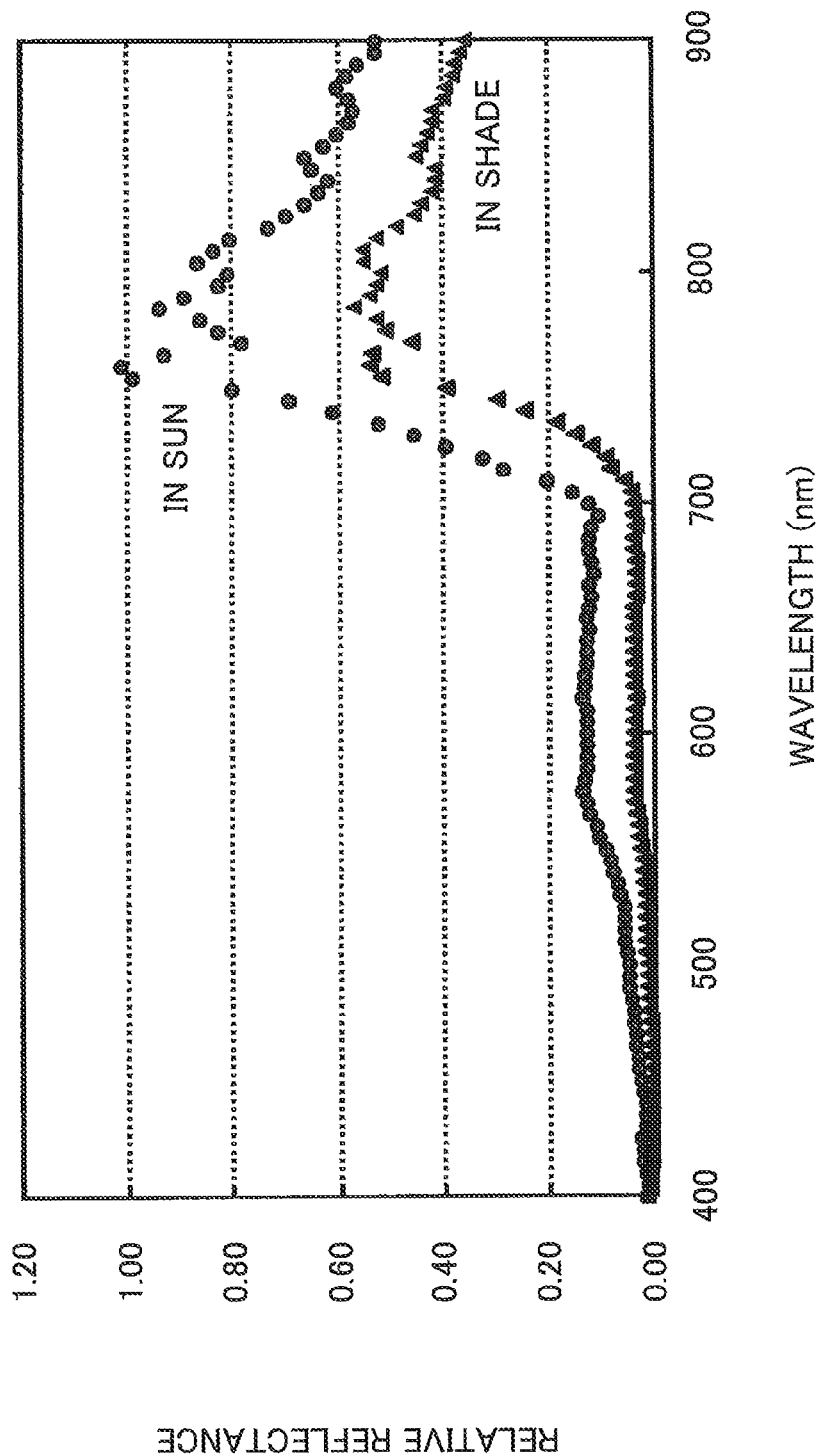
FIG. 2 is a diagram illustrating an example of reference spectral data stored in a reference data storage part in the embodiment.

FIG. 2 is a diagram illustrating an example of the reference spectral data stored in the reference data storage part 11.

The example illustrated in FIG. 2 depicts two area segments of the reference spectral data for the plant species *Pinus densiflora*, that is, the reflectance spectral data of the sunshine portion and the shaded portion. In the reflectance spectral data depicted in FIG. 2, values of relative reflectance for the sunlit portion (indicated as "IN SUN") are plotted with black circles and values of relative reflectance for the shaded portion (indicated as "IN SHADE") are plotted with black triangles.

Figure 3:
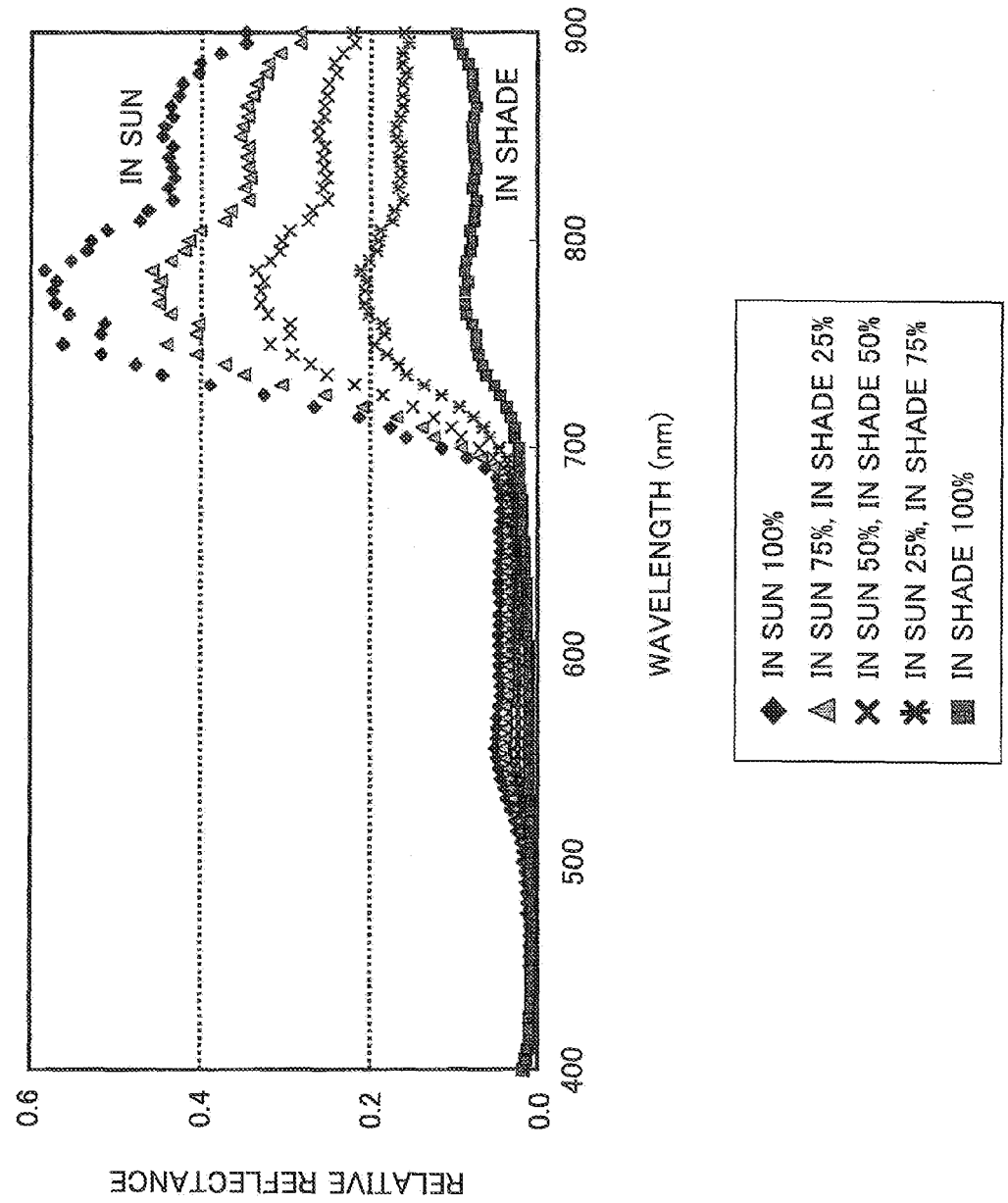
FIG. 3 is a diagram illustrating an example of the reference spectral data in a case of including a mixed portion in an area segment in the embodiment.

FIG. 3 is a diagram illustrating an example of the reference spectral data in a case of including the mixed portion in the area segment.

FIG. 3 depicts the reference spectral data of the sunlit portion ("IN SUN") and the shaded portion ("IN SHADE") of the same plant species and the reflectance spectral data for three types of the mixed portions predicted from these two sets of data.

In the reflectance spectral data depicted in FIG. 3, the values of the relative reflectance in the sunlit portion are plotted with black rhombuses, and the values of the relative reflectance in the shaded portion are plotted with black rectangles.

Also, the reference data generation part 14 generates three mixed portions: a first mixed portion (called "first mixtures") at a ratio of "the sunlit portion 75% and the shaded portion 25%", a second mixed portion (called "second mixtures") at a ratio of "the sunlit portion 50% and the shaded portion 50%", and a third mixed portion (called "third mixtures") at a ratio of "the sunlit portion 25% and the shaded portion 75%". The generated mixed portions are added to the reference data storage part 11. In the reflectance spectral data depicted in FIG. 3, the first mixtures are plotted as gray triangles, the second mixtures are plotted as cross marks, and the third mixtures are plotted as asterisks.

Next, a process of the plant species identification apparatus 1 will be briefly described.

Figure 4:
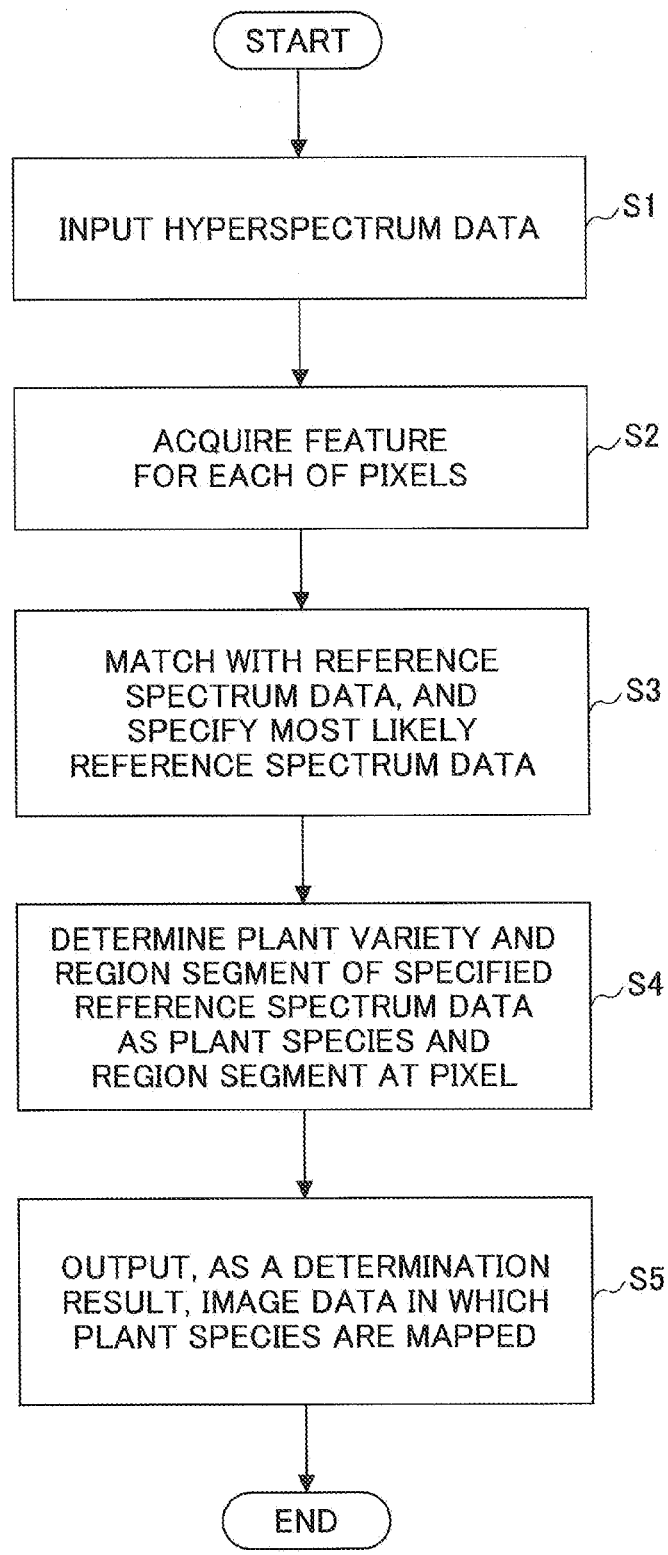
FIG. 4 is a diagram briefly illustrating a process flow example of the plant species identification apparatus in the embodiment.

FIG. 4 is a diagram briefly illustrating a process flow example of the plant species identification apparatus 1.

Step S1: the data input part 12 of the plant species identification apparatus 1 acquires the hyperspectral data 2 obtained at a location which is subject to the vegetation survey.

In the embodiment, as the hyperspectral data 2 to be input, the relative reflectance spectral data excluding influence of a light source or the maximum normalized relative reflectance are appropriately selected.

Step S2: the determination part 13 acquires the features of the reflectance spectral data for each of pixels in the hyperspectral data 2.

Step S3: the determination part 13 matches the reflectance spectral data of the pixels with the reference spectral data stored in the reference data storage part 11. The reference spectral data are classified by the plant species and the area segment. The determination part 13 specifies the most likely reference spectral data.

The determination part 13 may conduct a determination using the numeric value set calculated from the feature points of the spectral data as the above described first determination method, a determination in accordance with a Spectral Angle Mapper method, which is used by commercially available analytic software or the like in the market as the above described second determination method.

Step S4: the determination part 13 determines the plant species and the area segment where the specified reference spectral data are classified, as the plant species and the area segment of the pixel.

Step S5: the determination part 13 outputs as a determination result, for example, the image data 3 where a determination result (the plant species, or the plant species and area segment) with respect to each of pixels in the hyperspectral data 2 is mapped.

By this configuration, it is possible to automatically identify to which plant species, which are recorded in the reference data storage part 11, a pixel corresponds, for each of pixels from the hyperspectral data (image) 2 acquired at a subject location of the vegetation survey.

After that, since the reference spectral data (the reflectance spectral data) of the sunlit portion and the shaded portion, which are to be stored in the reference storage part 11, are used in the determination, it is possible to appropriately identify the plant species even for the shaded portion where the conventional correction does not properly identify the plant species.

Furthermore, since the reference spectral data of the mixed portion which are to be stored in the reference storage part 11, are used in the determination, it is possible to appropriately identify the plant species for the mixed portion in sun and shade.

Next, a determination process of the determination part 13 will be described in detail.

(1) First Determination Process Example

In a first determination process example, the numeric value set specific to the plant species and the area segment which are calculated based on the feature points appearing in the spectrum, as feature information of spectrum of a plant.

Figure 5:
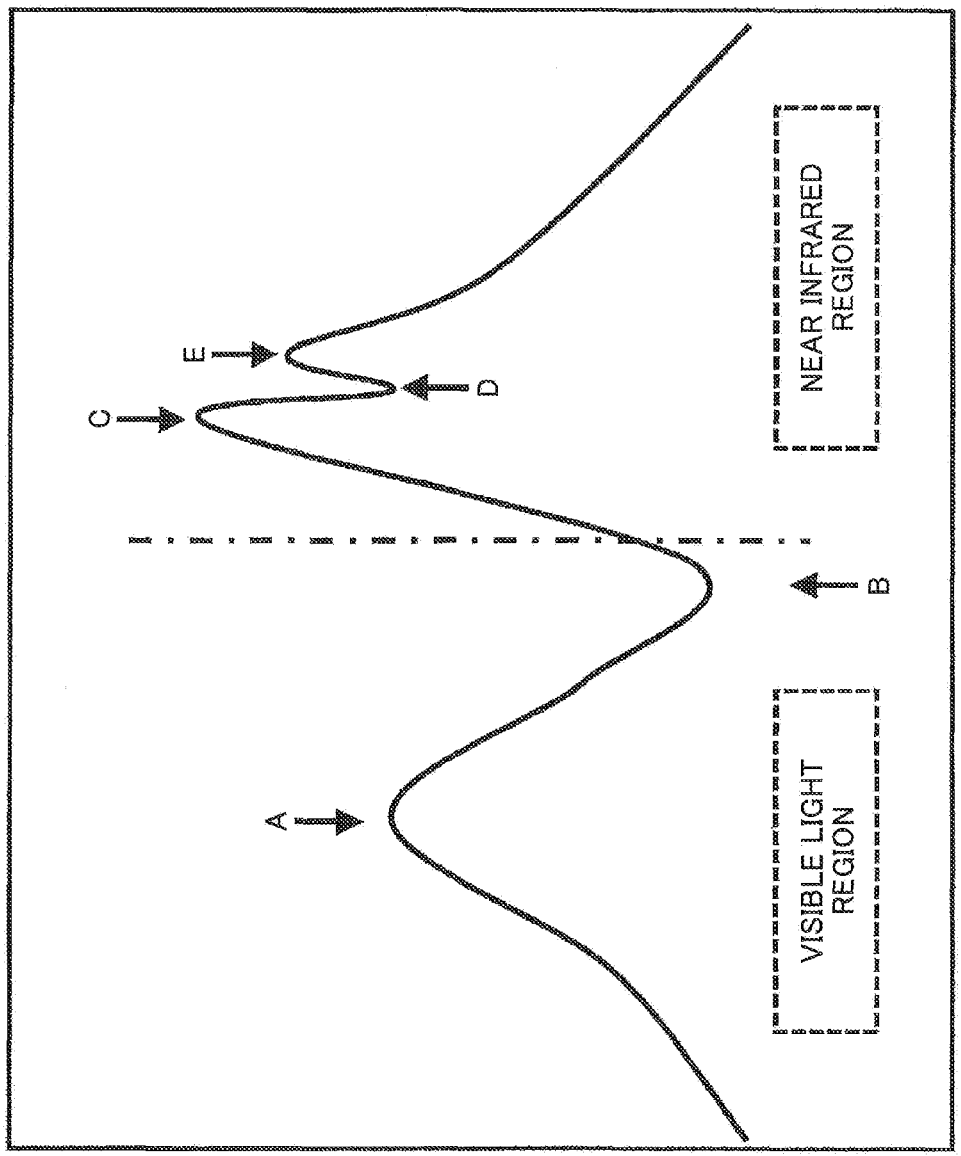
FIG. 5 is a diagram illustrating examples of feature points of the reflectance spectral data.

FIG. 5 is a diagram illustrating an example of the features points of the reflectance spectral data.

The spectrum of the plant is specific for each of the plant species, and may have a shape depicted in FIG. 5, for example. Therefore, there are feature points A through E such as a minimum value, a maximum value, and the like of a spectral curve in the reflectance spectral data.

The determination part 13 detects the feature points in the reference spectral data which are classified by the plant species and the area segment, determines multiple expressions (for example, a difference, a division, and the like) using more than two of the feature points, and acquires multiple calculated values (the numeric value set).

In the first determination process example, the determination part 13 calculates the numeric value set for each set of the reference spectral data stored in the reference data storage part 11.

FIG. 6 is a diagram illustrating an example of the numeric value set of the reference spectral data.

As depicted in FIG. 6, the numeric value set derived from the detected feature points is retained for each set of the reference spectral data classified by the plant species and the area segment.

In the embodiment, four percentages, a percentage (A/C) of the highest values, a slope (CB/AB), slope percentages HA/B)/(A/C), (CB/CD)/(CD/CE)), are used as the numeric value set.

FIG. 7A and FIG. 7B are diagrams illustrating concrete examples of the numeric value sets of the reference spectral data for each of the plant species.

In FIG. 7A, a numeric value set example of the reference spectral data, which are classified with the plant species and one area segment (the sunlit portion), is depicted. In FIG. 7B, a numeric value set example of the reference spectral data, which are classified with the plant species and multiple area segments (the sunlit portion, a portion mixing sunshine and shade at 50%, and the shaded portion), is depicted.

As seen from the examples illustrated in FIG. 7A and FIG. 7B, the numeric value set based on the feature points of the reflectance spectral data is specific for each of the plant species.

It is noted that details of a calculation process using the numeric value set of the reflectance spectral data are described in a specification of Japanese Patent Application No. 2011-074817 related to a technology invented by the inventor et al.

Similarly, the determination part 13 acquires the numeric value set for each of the pixels of the hyperspectral data 2, and specifies the numeric value set of the reference spectral data, a matching process, and the most likely reference spectral data.

Calculation for the numeric value set of the reference spectral data is executed before the determination process or during the determination process.

(2) Second Determination Process Example

In the second determination process, a determination is performed by a Spectral Angle Mapper method, and the feature vector of the spectral data is used as the feature information of the reflectance spectral data.

Figure 8:
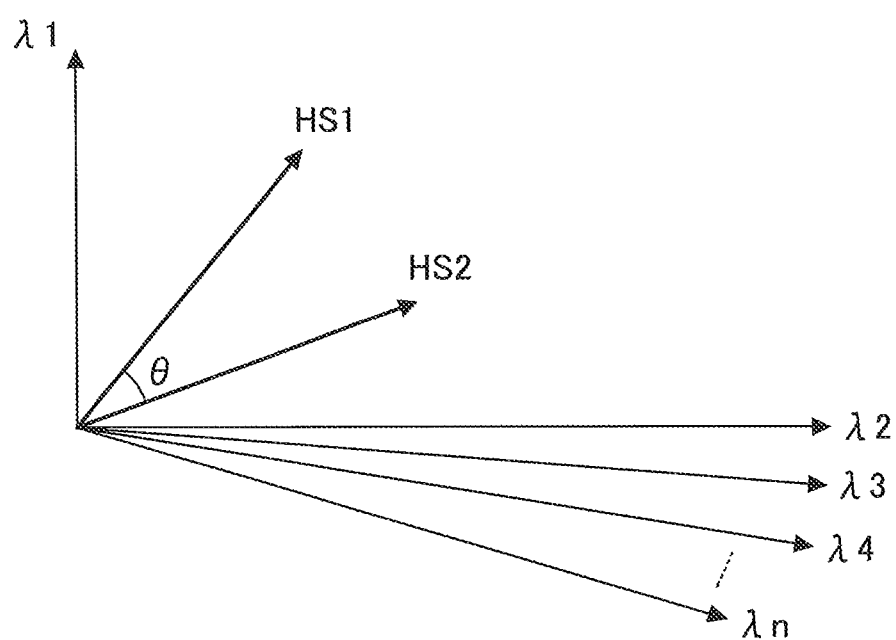
FIG. 8 is a conceptual diagram of matching similar vectors.

FIG. 8 is a conceptual diagram of matching similar vectors.

In the second determination process example, as illustrated in FIG. 8, the determination part 13 vectorizes the reflectance spectral data for each of the pixels of the hyperspectral data 2 and each set of the reference spectral data, and acquires similarity between the feature vector (eHS2) of the pixel and each set of the reference spectral data (eHS1) by a cosine distance (cos θ).

For example, the similarity (a similarity degree) among the feature vectors is calculated by the following expression. In the expression below, the closer the similarity is to 1, the more the reference spectral data are similar to reflectance spectral data.

$$\vec{HS} = R_1\vec{\lambda}_1 + R_2\vec{\lambda}_2 + R_3\vec{\lambda}_3 \ldots + R_n\vec{\lambda}_n$$

$$\cos\theta = \vec{eHS_1} \cdot \vec{eHS_2} \quad\quad \text{[formula 1]}$$

By this configuration, the reference spectral data, which are similar to the reflectance spectral data of the pixels, are specified.

Next, a detailed process example of the plant species identification apparatus 1 will be described.

Figure 9:
FIG. 9 is a diagram illustrating an example of the hyperspectral data (a hyperspectral image) taken from ground level at a subject location of a vegetation survey.

FIG. 9 is a diagram illustrating an example of the hyperspectral data (a hyperspectral image) taken from ground level at the subject location of the vegetation survey.

The hyperspectral data illustrated in FIG. 9 are regarded as an input of the plant species identification apparatus 1, and the identification of the plant species and the area segment is conducted.

The determination part 13 of the plant species identification apparatus 1 was performed by image analysis software (ENVI) for the remote sensing. Also, for comparison, two processes were performed respectively, in one case (a first case) of preparing a set of the reference spectral data (the sunlit portion) alone for each of the plant species and in another case (a second case) of preparing multiple area segments (the sunlit portion and the shaded portion) for each of the plant species, as the reference spectral data.

Figure 10A:
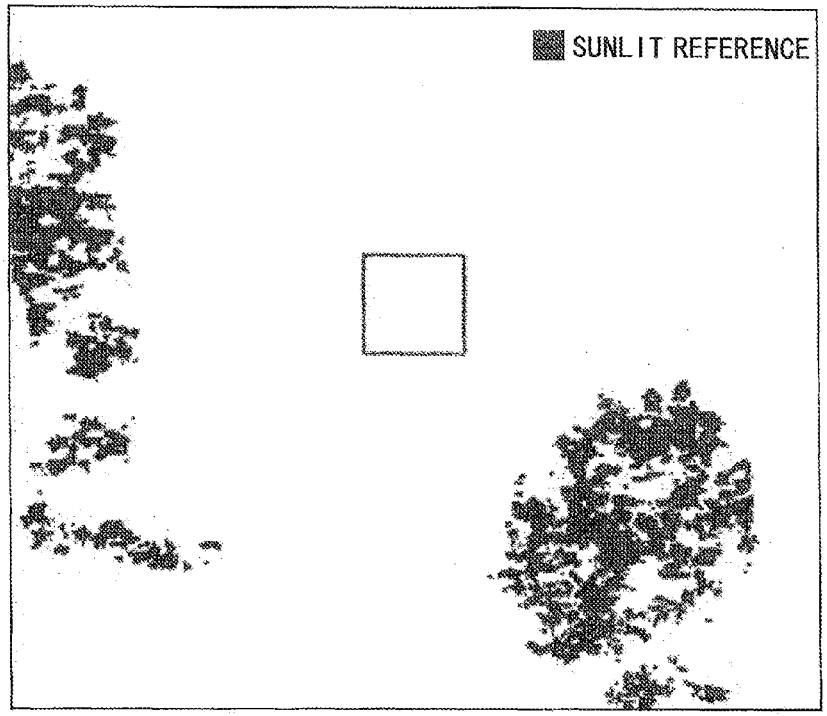
FIG. 10A is a diagram illustrating an image data example in which plants of the same species are mapped based on a determination result in a first case.

FIG. 10A is a diagram illustrating an image data example in which plants of the same species are mapped based on a determination result in the first case.

Figure 10B:
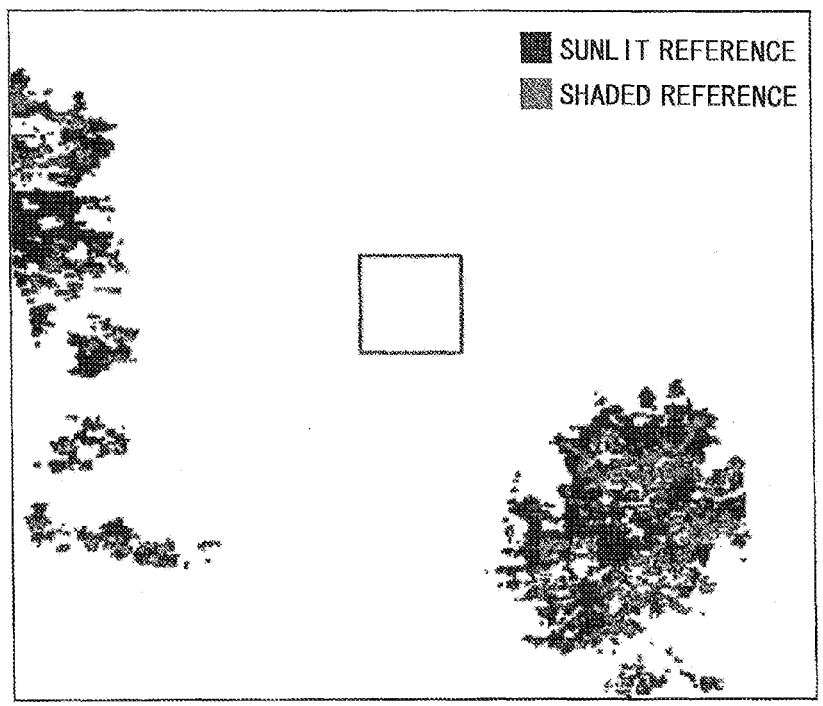
FIG. 10B is a diagram illustrating an image data example in which plants of the same species are mapped based on a determination result in a second case.

FIG. 10B is a diagram illustrating an image data example in which plants of the same species are mapped based on a determination result in the second case.

In the mapping for the image data depicted in FIG. 10B, more pixels are mapped than the mapping illustrated in FIG. 10A. Furthermore, as seen by referring to the image data in FIG. 9, a mapping result in FIG. 10B represents a state much closer to the current state than the mapping result in FIG. 10A. That is, as illustrated in FIG. 10B, identification accuracy is improved by the process of the plant species identification apparatus 1.

From the determination result illustrated in FIG. 10B, by using data of the mixed portion as the reference spectral data of the determination result, it is possible to further improve the identification accuracy of the plant species.

Next, a hardware configuration of the plant species identification apparatus 1 will be described.

Figure 11:
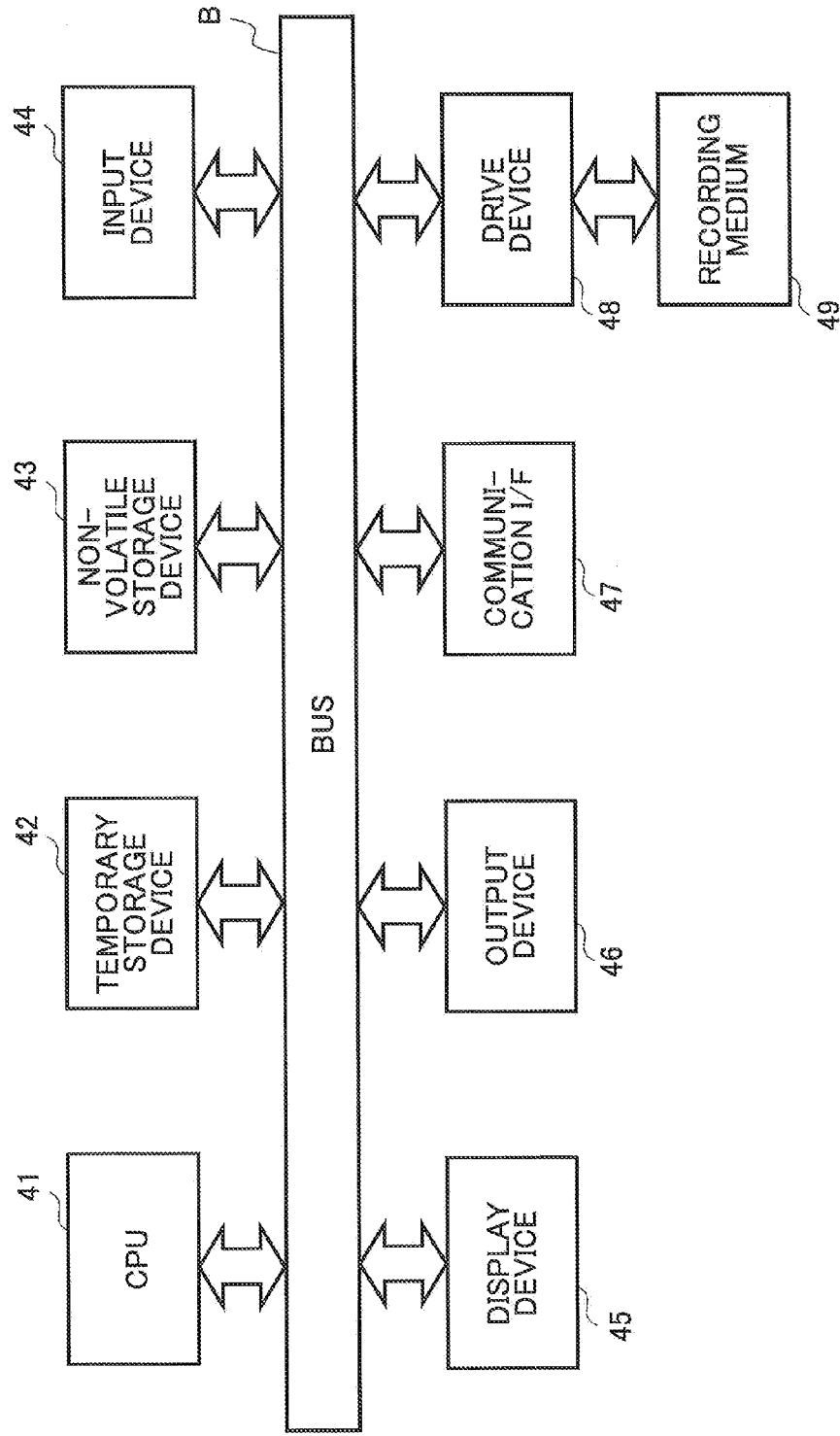
FIG. 11 is a hardware configuration of the plant species identification apparatus.

The plant species identification apparatus 1 is realized by a computer system including hardware including a CPU, a memory, and the like and a software program, or special hardware. That is, as illustrated in FIG. 11, the plant species identification apparatus 1 includes a CPU (Central Processing Unit) 41, a temporary storage device 42 such as a Dynamic Random Access Memory (DRAM), a flash memory, or the like, a non-volatile storage device 43 such as Hard Disk Drive (HDD), flash memory, or the like, an input device 44, a display device 45, an output device 46, a communication I/F 47, and a drive device 48, which are connected via a bus B. The plant species identification apparatus 1 is operable as a computer which inputs data from outside and outputs data to outside.

Also, it is possible that the plant species identification apparatus 1 may also be operated by a program executable for this computer. In this case, the program coding process contents of functions to be implemented in the plant species identification apparatus 1 are provided to the plant species identification apparatus 1. The provided program is executed by the computer, and the above described process functions of the plant species identification apparatus 1 are realized in the computer.

The CPU 41 controls the plant species identification apparatus 1 in accordance with the program stored in the temporary storage device 42. The temporary storage device 42 stores the program executed by the CPU 41, data used for the processing of the CPU 41, data acquired in the processing of the CPU 41, and the like.

The non-volatile storage device 43 stores data such as the program for performing various processes. A part of the program stored in the non-volatile storage device 43 is loaded in the temporary storage device 42, and is executed by the CPU 41, so that each of various processes is realized.

The above described reference data storage part 11 corresponds to a part of the temporary storage device 42 and/or the non-volatile storage device 43.

The input device 44 includes a mouse, a keyboard, and the like, and is used for a user to input each of various information items used in the process of the plant species identification apparatus 1. The display device 45 is used to display each of the various information items under control of the CPU 41. The output device 46 includes a printer and the like and is used to output each of the various information items in response to an instruction from the user. The communication I/F 47 is a device for controlling communications with an external device by connecting, for example, to the Internet, a LAN (Local Area Network), or the like.

The computer may read the program directly from a portable recording medium, and execute the process in accordance with the program. Furthermore, the program may be recorded in a computer-readable recording medium.

The program to realize the process conducted by the plant species identification apparatus 1 may be provided to the plant species identification apparatus 1 by a recording medium 49 such as a CD-ROM (Compact Disc Read-Only Memory). That is, when the recording medium 49 storing the program is set in the drive device 48, the drive device 48 reads out the program from the recording medium 49. The program being read out is installed into the non-volatile storage device 43 through the bus B. After that, when the program is activated, the CPU 41 begins the process in accordance with the program installed into the non-volatile storage device 43. A medium for storing the program is not limited to the CD-ROM, and may be the computer-readable recording medium. As the computer-readable recording medium 49, a portable recording medium such as a DVD disk, a USB memory or the like, or a semiconductor memory such as a flash memory, as well as the CD-ROM may be used.

As described above, according to the plant species identification apparatus 1, by using multiple sets of reference data corresponding to the plant species and the area segment, in particular, two sets of the reference spectral data: the sunlit portion and the shaded portion, it is possible to realize an automatic identification for the plant species with respect to a portion that was not able to be identified conventionally. Hence, according to the plant species identification apparatus 1, it is possible to easily identify the plant species without depending on the experience of an identification person.

The present invention is not limited to the specifically disclosed embodiments, and variations and modifications may be made without departing from the scope of the invention.

All examples and conditional language recited herein are intended for pedagogical purposes to aid the reader in understanding the invention and the concepts contributed by the inventors to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A plant species identification apparatus for identifying plant species, the apparatus comprising a processor configured to perform a process including:
   storing reference spectral data which indicate a reflectance spectral feature classified by area segments including a sunlit portion and a shaded portion in addition to the plant species, to a reference data storage part;
   predicting, from the reference data storage part, a reflectance spectrum of an area where the sunlit portion and the shaded portion are mixed at a predetermined ratio based on the reference spectral data that are for a same plant species and that are classified into the area segments including the sunlit portion and the shaded portion, classifying a set of the reference spectral data indicating a predicted reflectance spectral feature into the same plant species and a mixed portion of the area segment, and adding the set of the reference spectral data to the reference data storage part;
   acquiring hyperspectral data to be a target;
   specifying most similar reference spectral data to a feature of reflectance spectrum of a pixel for each of pixels of the hyperspectral data from the reference data storage part; and
   determining the plant species of the pixels based on a classification of the reference spectral data.

2. The plant species identification apparatus as claimed in claim 1, wherein:
   the specifying is configured to extract feature points of the reflectance spectrum of the pixel for each of the pixels, and to acquire a numeric value set of the pixel by calculating values of the feature points being extracted using multiple expressions, and is further configured to extract the feature points from each set of the reference spectral data stored in the reference data storage part, to compare a specific numeric value set for the plant species and the area segment, which is acquired by calculating the values of the feature points being extracted by the multiple expressions, with the numeric value set of the pixel, and to specify the reference spectral data having a most similar numeric value set.

3. The plant species identification apparatus as claimed in claim 2, wherein the numeric value set is calculated by using the values of the feature points corresponding to multiple wavelengths in the hyperspectral data.

4. The plant species identification apparatus as claimed in claim 1, wherein the specifying is configured to acquire a feature vector of the reflectance spectrum of the pixel, and is further configured to compare the feature vector of the reflectance spectrum of each set of the reference spectrum stored in the reference data storage part with the feature vector of the pixel, and to specify the reference spectral data having a most similar feature vector.

5. The plant species identification apparatus as claimed in claim 1, wherein values corresponding to the wavelengths in the hyperspectral data.

6. A method performed in a computer to identify the plant species, the method comprising:
   storing reference spectral data which indicate a reflectance spectral feature classified by area segments including a sunlit portion and a shaded portion in addition to the plant species, to a reference data storage part;
   predicting, from the reference data storage part, a reflectance spectrum of an area where the sunlit portion and the shaded portion are mixed at a predetermined ratio based on the reference spectral data that are for a same plant species and that are classified into the area segments including the sunlit portion and the shaded portion, classifying a set of the reference spectral data indicating a predicted reflectance spectral feature into the same plant species and a mixed portion of the area segment, and adding the set of the reference spectral data to the reference data storage part;

acquiring hyperspectral data to be a target;

specifying most similar reference spectral data to a feature of reflectance spectrum of a pixel from the reference data storage part for each of pixels of the hyperspectral data; and determining the plant species of the pixels based on a classification of a specified reference spectral data.

7. A non-transitory computer-readable medium storing a program that causes a computer to execute a process comprising:

storing reference spectral data which indicate a reflectance spectral feature classified by area segments including a sunlit portion and a shaded portion in addition to the plant species, to a reference data storage part;

predicting, from the reference data storage part, a reflectance spectrum of an area where the sunlit portion and the shaded portion are mixed at a predetermined ratio based on the reference spectral data that are for a same plant species and that are classified into the area segments including the sunlit portion and the shaded portion, classifying a set of the reference spectral data indicating a predicted reflectance spectral feature into the same plant species and a mixed portion of the area segment, and adding the set of the reference spectral data to the reference data storage part;

acquiring hyperspectral data to be a target;

specifying most similar reference spectral data to a feature of reflectance spectrum of a pixel from the reference data storage part for each of pixels of the hyperspectral data; and determining the plant species of the pixels based on a classification of a specified reference spectral data.

\* \* \* \* \*